United States Patent
Kojima (10) Patent No.: US 12,089,818 B2
(45) Date of Patent: Sep. 17, 2024

(54) LIGHT SOURCE CONTROL DEVICE AND MEDICAL OBSERVATION SYSTEM

(71) Applicant: Sony Olympus Medical Solutions Inc., Tokyo (JP)

(72) Inventor: Koji Kojima, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 0 days.

(21) Appl. No.: 17/498,768

(22) Filed: Oct. 12, 2021

(65) Prior Publication Data
US 2022/0160219 A1    May 26, 2022

(30) Foreign Application Priority Data
Nov. 20, 2020  (JP) ................ 2020-193846

(51) Int. Cl.
| | | |
|---|---|---|
| A61B 1/06 | (2006.01) | |
| A61B 1/04 | (2006.01) | |
| A61B 1/045 | (2006.01) | |

(52) U.S. Cl.
CPC ............ *A61B 1/0638* (2013.01); *A61B 1/045* (2013.01); *A61B 1/042* (2013.01); *A61B 1/0669* (2013.01)

(58) Field of Classification Search
CPC ..... A61B 1/00009; A61B 1/043; A61B 1/045; A61B 1/0638; A61B 1/0684; H04N 5/2256; H04N 5/3532; H04N 2005/2255; H04N 25/531
See application file for complete search history.

(56) References Cited

U.S. PATENT DOCUMENTS

| | | | | |
|---|---|---|---|---|
| 2009/0059046 A1* | 3/2009 | Hasegawa | ............... | H04N 23/74 348/E5.091 |
| 2011/0109761 A1* | 5/2011 | Shimotsu | ............... | H04N 23/74 348/222.1 |
| 2013/0201315 A1* | 8/2013 | Takei | ..................... | A61B 1/045 348/77 |
| 2014/0163319 A1* | 6/2014 | Blanquart | ............ | H04N 25/531 600/109 |
| 2015/0116561 A1* | 4/2015 | Takei | ..................... | G03B 15/05 348/296 |
| 2017/0064178 A1* | 3/2017 | Kagawa | .............. | G02B 23/2469 |
| 2019/0320886 A1* | 10/2019 | Yano | ................... | G02B 23/2461 |
| 2022/0007925 A1* | 1/2022 | Stith | .................... | H04N 25/131 |

FOREIGN PATENT DOCUMENTS

WO   2020/170669 A1   8/2020

* cited by examiner

*Primary Examiner* — Anh Tuan T Nguyen
*Assistant Examiner* — Shankar Raj Ghimire
(74) *Attorney, Agent, or Firm* — XSENSUS LLP (57) ABSTRACT

A light source control device includes a light source controller configured to: cause a first light source to emit light in a visible wavelength band in a first entire line exposure period, which is an entire line exposure period in which all horizontal lines in an effective pixel area are simultaneously exposed; cause a second light source to emit excitation light in a second entire line exposure period, which is different from the first entire line exposure period; and cause the excitation light to be emitted in an excitation light emission period including the second entire line exposure period and a period, which is adjacent to the second entire line exposure period and is at least a part of a readout period during which charges accumulated in the plurality of pixels are read out, when controlling an operation of the second light source.

20 Claims, 6 Drawing Sheets

LIGHT SOURCE CONTROL DEVICE AND MEDICAL OBSERVATION SYSTEM

CROSS-REFERENCE TO RELATED APPLICATION

This application claims priority from Japanese Application No. 2020-193846, filed on Nov. 20, 2020, the contents of which are incorporated by reference herein in its entirety.

BACKGROUND

The present disclosure relates to a light source control device and a medical observation system.

In the related art, there is known a medical observation system that captures an observation target in a living body or the like using a complementary metal oxide semiconductor (CMOS), which is a rolling shutter type image sensor, and observes the observation target (see, for example, WO 2020/170669).

In the medical observation system described in WO 2020/170669, a normal light image and a fluorescence image are generated. Specifically, the normal light image is an image obtained by irradiating the observation target with normal light in a visible wavelength band to capture the normal light transmitted through the observation target. In addition, the fluorescence image is an image obtained by irradiating the observation target with excitation light to capture fluorescence from the observation target excited by the excitation light.

Here, in the medical observation system described in WO 2020/170669, the normal light and the excitation light are emitted only in the entire line exposure period in which all horizontal lines in an effective pixel area in the image sensor are simultaneously exposed, in order to suppress luminance unevenness in the normal light image and the fluorescence image.

SUMMARY

Meanwhile, a signal level is remarkably low in the fluorescence image because the fluorescence from the observation target is minute and the sensitivity of the image sensor in a wavelength band of the fluorescence is also low. Therefore, there is a problem that it is difficult to generate an image suitable for observation.

According to one aspect of the present disclosure, there is provided a light source control device including a light source controller configured to: cause a first light source to emit light in a visible wavelength band in a first entire line exposure period, which is an entire line exposure period in which all horizontal lines in an effective pixel area are simultaneously exposed, in a rolling shutter type image sensor in which a plurality of pixels are two-dimensionally arrayed in units of the horizontal lines; cause a second light source to emit excitation light in a second entire line exposure period, which is the entire line exposure period different from the first entire line exposure period; and cause the excitation light to be emitted in an excitation light emission period including the second entire line exposure period and a period, which is adjacent to the second entire line exposure period and is at least a part of a readout period during which charges accumulated in the plurality of pixels are read out, when controlling an operation of the second light source.

DETAILED DESCRIPTION

Hereinafter, modes (hereinafter, embodiments) for carrying out the present disclosure will be described with reference to the drawings. Note that the present disclosure is not limited to the embodiments to be described below. Further, the same parts are denoted by the same reference signs when the drawings are described.

First Embodiment

Schematic Configuration of Medical Observation System

Figure 1:
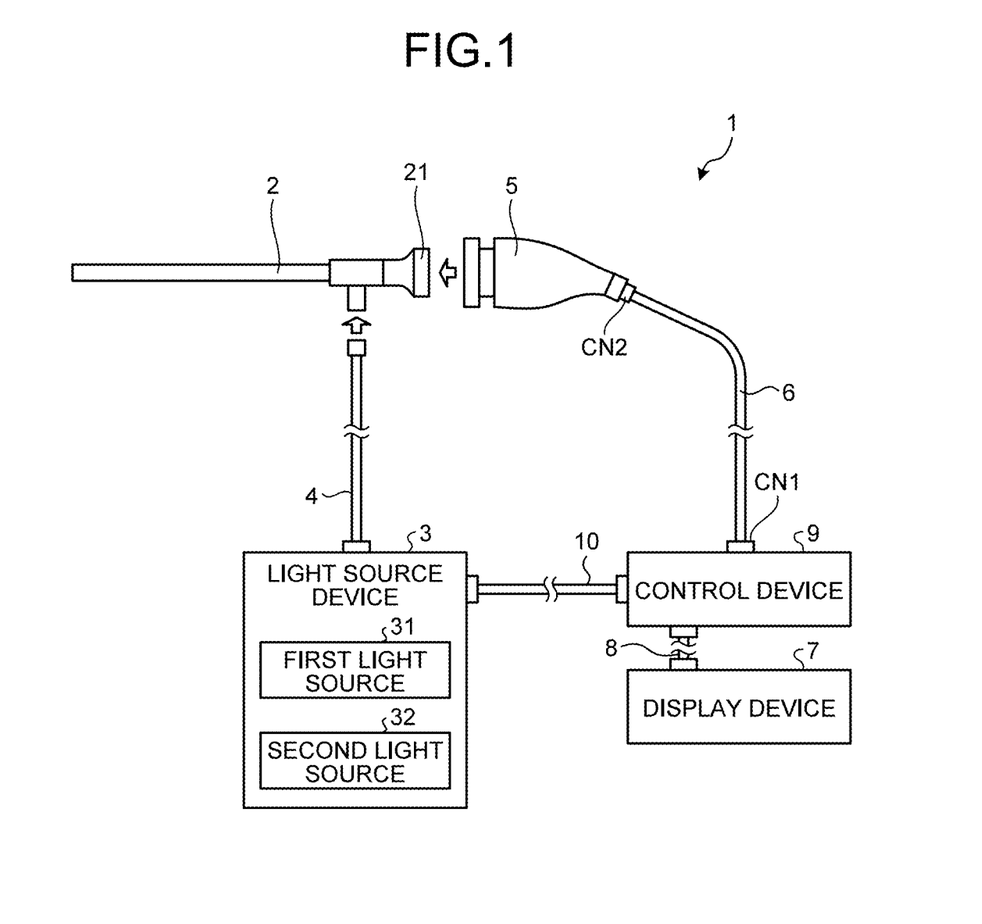
FIG. 1 is a diagram illustrating a configuration of a medical observation system according to a first embodiment.

FIG. 1 is a diagram illustrating a configuration of a medical observation system 1 according to a first embodiment.

The medical observation system 1 is a system that is used in the medical field and captures (observes) the inside of a living body (observation target) that is a subject. As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

In the first embodiment, the insertion unit 2 includes a rigid endoscope. That is, the insertion unit 2 has an elongated shape that is entirely rigid or has a part that is soft and the other part that is rigid, and is inserted into the living body. An optical system, which is configured using one or a plurality of lenses and condenses light from the subject, is provided in the insertion unit 2.

The light source device 3 is connected with one end of the light guide 4, and supplies light to the one end of the light guide 4 to irradiate the inside of the living body under control of the control device 9. As illustrated in FIG. 1, the light source device 3 includes a first light source 31 and a second light source 32.

The first light source 31 generates (emits) normal light in a visible wavelength band. In the first embodiment, the first light source 31 includes a light emitting diode (LED) that emits white light.

The second light source 32 generates (emits) excitation light having a wavelength band different from the wavelength band of normal light. In the first embodiment, the second light source 32 includes a semiconductor laser or an LED that emits near-infrared excitation light in a near-infrared wavelength band (for example, a wavelength band of about 750 nm to 800 nm). The near-infrared excitation light is excitation light that excites a fluorescent substance such as indocyanine green. In addition, when being excited by the near-infrared excitation light, the fluorescent substance, such as indocyanine green, emits fluorescence in a wavelength band (for example, a wavelength band around 830 nm), other than the visible range, which has a central wavelength on the longer wavelength side than a central wavelength of the wavelength band of the near-infrared excitation light. Note that the wavelength band of the near-infrared excitation light and the wavelength band of the fluorescence may be set so as to partially overlap each other, or may be set so as not to overlap each other at all.

Further, the first light source 31 is driven during a first period between alternately repeated first and second periods under control of the control device 9 in the light source device 3 according to the first embodiment. That is, the light source device 3 emits normal light (white light) during the first period. In addition, the second light source 32 is driven during the second period under the control of the control device 9 in the light source device 3. That is, the light source device 3 emits near-infrared excitation light during the second period.

Note that the light source device 3 is configured separately from the control device 9 in the first embodiment, but the present disclosure is not limited thereto and may adopt a configuration in which the light source device 3 is provided inside the control device 9.

The one end of the light guide 4 is detachably connected to the light source device 3, and the other end thereof is detachably connected to the insertion unit 2. Further, the light guide 4 transmits light (normal light or near-infrared excitation light) supplied from the light source device 3 from the one end to the other end, and supplies the light to the insertion unit 2. When the inside of the living body is irradiated with the normal light (white light), the normal light transmitted through the living body (normal light reflected in the living body) is condensed by the optical system in the insertion unit 2. In addition, when the inside of a living body is irradiated with the near-infrared excitation light, the near-infrared excitation light passing through the living body (near-infrared excitation light reflected in the living body) and fluorescence emitted from a fluorescent substance as the fluorescent substance, such as indocyanine green, accumulated at a lesion in the living body is excited by the near-infrared excitation light, are condensed by an optical system in the insertion unit 2.

The camera head 5 corresponds to an imaging device according to the present disclosure. The camera head 5 is detachably connected to a proximal end (an eyepiece portion 21 (FIG. 1)) of the insertion unit 2. Further, the camera head 5 captures the light condensed by the insertion unit 2 to generate a captured image under the control of the control device 9.

Note that a detailed configuration of the camera head 5 will be described in "Configuration of Camera Head" which will be described later.

The first transmission cable 6 has one end detachably connected to the control device 9 via a connector CN1 (FIG. 1), and the other end detachably connected to the camera head 5 via a connector CN2 (FIG. 1). Further, the first transmission cable 6 transmits the captured image and the like output from the camera head 5 to the control device 9, and transmits a control signal, a synchronization signal, a clock, power, and the like output from the control device 9 to the camera head 5.

Note that the captured image and the like may be transmitted as an optical signal or may be transmitted as an electrical signal in the transmission of the captured image and the like from the camera head 5 to the control device 9 via the first transmission cable 6. The same applies to the transmission of the control signal, the synchronization signal, and the clock from the control device 9 to the camera head 5 via the first transmission cable 6.

The display device 7 includes a display using liquid crystal, organic electro luminescence (EL), or the like, and displays an image based on a video signal from the control device 9 under the control of the control device 9.

The second transmission cable 8 has one end detachably connected to the display device 7 and the other end detachably connected to the control device 9. Further, the second transmission cable 8 transmits the video signal processed by the control device 9 to the display device 7.

The control device 9 corresponds to a light source control device according to the present disclosure. The control device 9 includes a central processing unit (CPU), a field-programmable gate array (FPGA), and the like, and integrally controls operations of the light source device 3, the camera head 5, and the display device 7.

Note that a detailed configuration of the control device 9 will be described in "Configuration of Control Device" which will be described later.

The third transmission cable 10 has one end detachably connected to the light source device 3 and the other end detachably connected to the control device 9. Further, the third transmission cable 10 transmits a control signal from the control device 9 to the light source device 3.

Configuration of Camera Head

Next, the configuration of the camera head 5 will be described.

Figure 2:
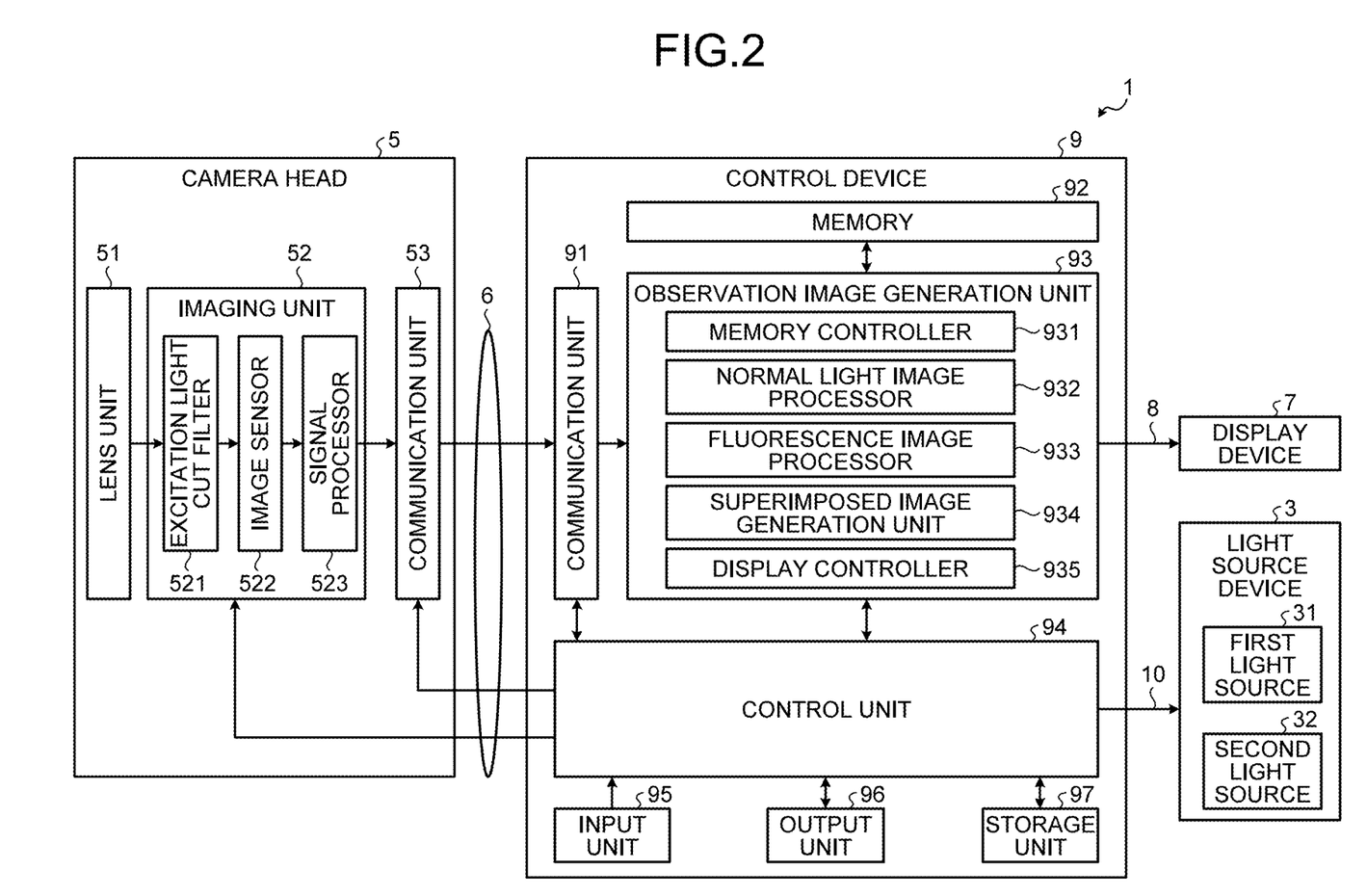
FIG. 2 is a block diagram illustrating configurations of a camera head and a control device.

FIG. 2 is a block diagram illustrating the configurations of the camera head 5 and the control device 9.

As illustrated in FIG. 2, the camera head 5 includes a lens unit 51, an imaging unit 52, and a communication unit 53.

The lens unit 51 is configured using one or a plurality of lenses, and forms an image of light (normal light, near-infrared excitation light, or fluorescence) condensed by the insertion unit 2 on an imaging surface of the imaging unit 52 (image sensor 522).

The imaging unit 52 captures the inside of a living body under control of the control device 9. As illustrated in FIG. 2, the imaging unit 52 includes an excitation light cut filter 521, the image sensor 522, and a signal processor 523.

The excitation light cut filter 521 is provided between the lens unit 51 and the image sensor 522, and includes a band stop filter that removes a specific wavelength band. Note that, hereinafter, a wavelength band to be cut (removed) by the excitation light cut filter 521 will be referred to as a cut band, a wavelength band that is closer to a short wavelength side than the cut band and is transmitted through the excitation light cut filter 521 will be referred to as a short-wavelength-side transmission area, and a wavelength band that is closer to a long wavelength side than the cut band and is transmitted through the excitation light cut filter 521 will be referred to as a long-wavelength-side transmission area, for convenience of the description.

Here, the cut band includes at least a part of the wavelength band of near-infrared excitation light. In the first embodiment, the cut band includes the entire wavelength band of the near-infrared excitation light. In addition, a long-wavelength-side transmission band includes the wavelength band of fluorescence. Further, the short-wavelength-side transmission area includes the wavelength band of normal light (white light).

That is, the excitation light cut filter 521 transmits normal light (white light) directed from the lens unit 51 to the image sensor 522. Note that, hereinafter, the normal light (white light) that is transmitted through the excitation light cut filter 521 and directed to the image sensor 522 will be referred to as a subject image for convenience of the description. On the other hand, the excitation light cut filter 521 removes near-infrared excitation light and transmits fluorescence for the near-infrared excitation light and the fluorescence directed from the lens unit 51 to the image sensor 522. Note that, hereinafter, the fluorescence that is transmitted through the excitation light cut filter 521 and directed to the image sensor 522 will be referred to as a fluorescent image for convenience of the description.

The image sensor 522 receives the subject image or the fluorescent image transmitted through the excitation light cut filter 521 and converts the received image into an electrical signal (analog signal). In the first embodiment, the image sensor 522 includes a CMOS that is a rolling shutter type image sensor in which a plurality of pixels are two-dimensionally arrayed in units of horizontal lines.

Here, the image sensor 521 includes an ineffective area that is not electrically guaranteed, an optical black area (OB area), and an effective pixel area that converts a subject image formed by the lens unit 51 into an imaging signal and outputs the imaging signal although not specifically illustrated.

Further, the image sensor 522 performs imaging every first and second periods, which are alternately repeated, in synchronization with light emission timings of the light source device 3 under the control of the control device 9. Hereinafter, for convenience of the description, an image generated by capturing the subject image (normal light) during the first period by the image sensor 522 will be referred to as a normal light image, and an image generated by capturing the fluorescent image (fluorescence) during the second period by the image sensor 522 will be referred to as a fluorescence image. In addition, the normal light image and the fluorescence image are collectively referred to as a captured image.

The signal processor 523 performs signal processing on a captured image of an analog signal generated by the image sensor 522 and outputs a captured image of a digital signal.

The communication unit 53 functions as a transmitter that transmits the captured image output from the imaging unit 52 to the control device 9 via the first transmission cable 6. The communication unit 53 includes, for example, a high-speed serial interface that performs communication of the captured image at a transmission rate of 1 Gbps or more with the control device 9 via the first transmission cable 6.

Configuration of Control Device

Next, the configuration of the control device 9 will be described with reference to FIG. 2.

As illustrated in FIG. 2, the control device 9 includes a communication unit 91, a memory 92, an observation image generation unit 93, a control unit 94, an input unit 95, an output unit 96, and a storage unit 97.

The communication unit 91 functions as a receiver that receives a captured image output from the camera head 5 (communication unit 53) via the first transmission cable 6. The communication unit 91 includes, for example, a high-speed serial interface that performs communication of the captured image with the communication unit 53 at a transmission rate of 1 Gbps or more. That is, the communication unit 91 corresponds to an image acquisition unit according to the present disclosure.

The memory 92 includes, for example, a dynamic random access memory (DRAM) or the like. The memory 92 may temporarily store a plurality of frames of captured images sequentially output from the camera head 5 (communication unit 53).

The observation image generation unit 93 processes the captured images sequentially output from the camera head 5 (communication unit 53) and received by the communication unit 91 under control of the control unit 94. As illustrated in FIG. 2, the observation image generation unit 93 includes a memory controller 931, a normal light image processor 932, a fluorescence image processor 933, a superimposed image generation unit 934, and a display controller 935.

The memory controller 931 controls write and readout of the captured image to and from the memory 92. More specifically, the memory controller 931 sequentially writes the captured images (normal light image and fluorescence image), sequentially output from the camera head 5 (communication unit 53) and received by the communication unit 91, into the memory 92. In addition, the memory controller 931 reads out a normal light image from the memory 92 at a specific timing, and inputs the readout normal light image to the normal light image processor 932. Further, the memory controller 931 reads out the fluorescence image from the memory 92 at a specific timing, and inputs the read fluorescence image to the fluorescence image processor 933.

The normal light image processor 932 executes first image processing on the input normal light image.

Examples of the first image processing may include optical black subtraction processing, white balance adjustment processing, demosaic processing, and color correction matrix processing, gamma correction processing, and YC processing for converting an RGB signal (normal light image) into a luminance/color difference signal (Y, Cb/Cr signal).

The fluorescence image processor 933 performs second image processing different from the first image processing on the input fluorescence image.

Examples of the second image processing may include optical black subtraction processing, white balance adjustment processing, demosaic processing, and color correction matrix processing, gamma correction processing, and YC processing for converting an RGB signal (fluorescence image) into a luminance/color difference signal (Y, Cb/Cr signal), which is similar to the first image processing described above.

The superimposed image generation unit 934 executes superimposition processing for superimposing the fluorescence image on which the second image processing has been executed by the fluorescence image processor 933 on the normal light image on which the first image processing has been executed by the normal light image processor 932 to generate a superimposed image.

Here, as the superimposition processing, first and second superimposition processes to be described below may be exemplified. Note that, hereinafter, an area, which includes a pixel whose luminance value is a specific threshold or more, in a fluorescence image will be referred to as a fluorescence area.

The first superimposition process is a process of replacing an area at the same pixel position as a fluorescence area in a normal light image with an image of the fluorescence area in a fluorescence image.

The second superimposition process is a process (so-called alpha blend process) of changing brightness of a color indicating fluorescence applied to each pixel in an area at the same pixel position as a fluorescence area in a normal light image according to a luminance value at each pixel position in the fluorescence area of a fluorescence image.

The display controller 935 generates a video signal for displaying the superimposed image generated by the superimposed image generation unit 934 under the control of the control unit 94. Further, the display controller 935 outputs the video signal to the display device 7 via the second transmission cable 8.

The control unit 94 is configured using, for example, a CPU, an FPGA, or the like, and outputs a control signal via the first to third transmission cables 6, 8, and 10, thereby controlling the operations of the light source device 3, the camera head 5, and the display device 7 and controlling the overall operation of the control device 9. The control unit 94 has a function as a light source controller according to the present disclosure. Note that functions of the light source controller will be described in "Operation of Control Device" which will be described later.

The input unit 95 is configured using an operation device such as a mouse, a keyboard, and a touch panel, and receives a user operation from a user such as a doctor. Further, the input unit 95 outputs an operation signal corresponding to the user operation to the control unit 94.

The output unit 96 is configured using a speaker, a printer, or the like, and outputs various types of information.

The storage unit 97 stores a program executed by the control unit 94, information necessary for processing of the control unit 94, and the like.

Operation of Control Device

Next, the operation of the control device 9 will be described.

Note that control of the image sensor 522 by the control unit 94 (hereinafter, referred to as imaging control) and control of the first and second light sources 31 and 32 by the control unit 94 (hereinafter, referred to as light source control) will be mainly described hereinafter for convenience of the description.

Figure 3:
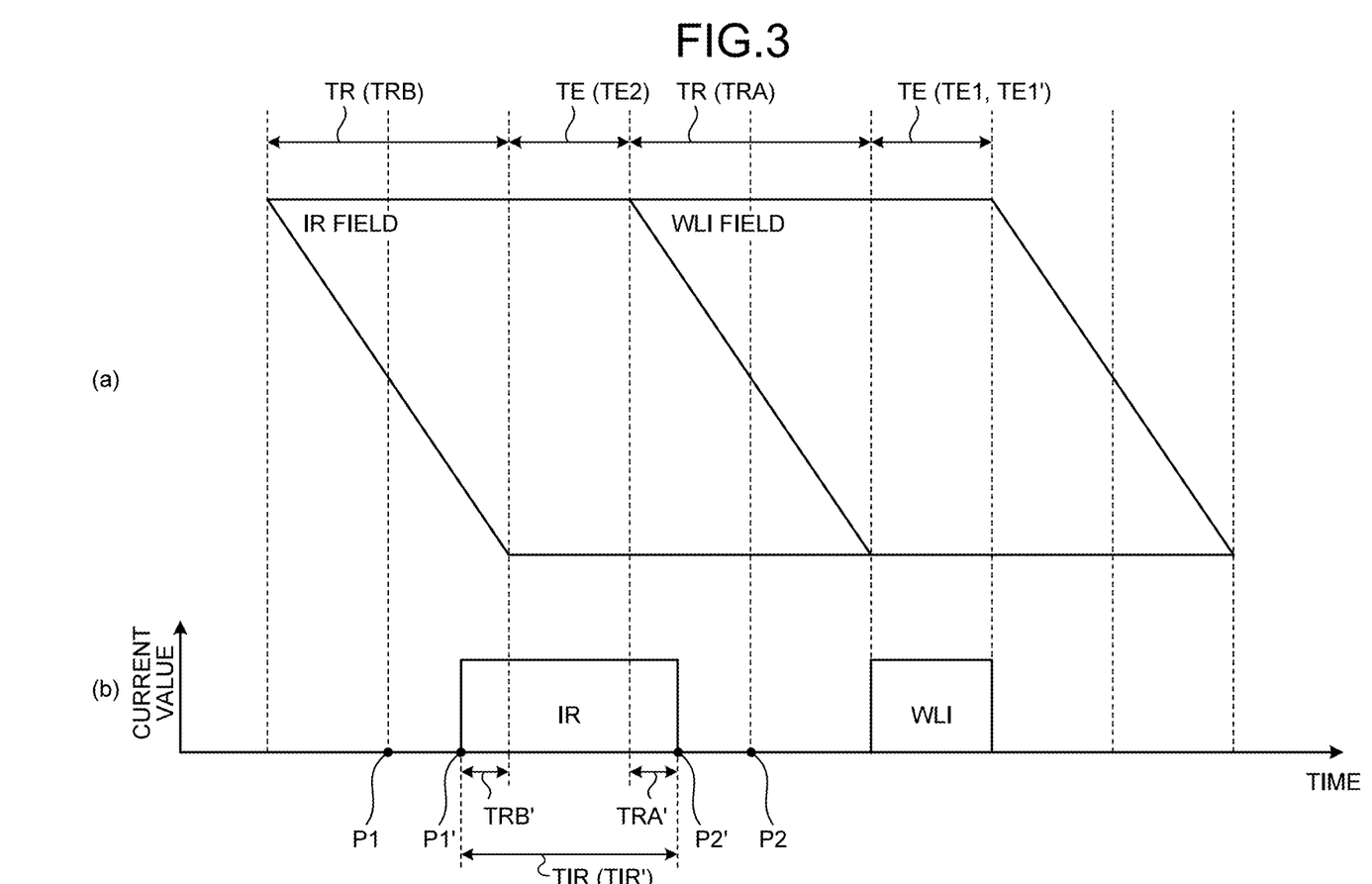
FIG. 3 is a view for describing an operation of the control device.

FIG. 3 is a view for describing the operation of the control device 9. Specifically, FIG. 3(a) is a view illustrating exposure timings of the image sensor 522, where the vertical axis represents the horizontal line of the image sensor 522 (the uppermost line indicates the uppermost horizontal line (the first horizontal line), and the lowermost line indicates the lowermost horizontal line (the last line)), and the horizontal axis represents time. Note that, in FIG. 3(a), a parallelogram area contributing to generation of a normal light image is described as a white light imaging (WLI) field, and a parallelogram area contributing to generation of a fluorescence image is described as an infra-red (IR) field. FIG. 3(b) is a view illustrating light source control, where the vertical axis represents current values supplied to the first and second light sources 31 and 32, and the horizontal axis represents time (applied pulse widths of currents supplied to first and second light sources 31 and 32 (current supply times)). Note that the current value and the current supply time are actually changed based on the brightness (an average value of luminance values or the like) of a specific area (detection area) in a normal light image or a fluorescence image in the light source control, but FIG. 3(b) illustrates a case where the current value is maximized and the current supply time is maximized for convenience of the description. In addition, in FIG. 3(b), emission of normal light is described as WLI, and emission of excitation light is described as IR.

First, the imaging control is performed as follows.

The control unit 94 performs exposure control according to a so-called rolling shutter scheme in which exposure of the image sensor 522 in one frame period is started sequentially for each horizontal line and readout is performed sequentially for each horizontal line for which a predetermined period (so-called shutter speed) has elapsed from the start of exposure. In the first embodiment, the control unit 94 performs exposure control such that one frame period includes an entire line exposure period TE in which all horizontal lines in an effective pixel area in the image sensor 522 are simultaneously exposed and a readout period TR for reading out charges accumulated in the plurality of pixels of the image sensor 522 as illustrated in FIG. 3(a).

Next, the light source control is performed as follows.

As illustrated in FIG. 3(b), the control unit 94 alternately repeats light emission of the first light source 31 and light emission of the second light source 32.

Specifically, when operating the first light source 31, the control unit 94 causes the first light source 31 to emit light during a whole first period TE1' within an entire line exposure period TE1 in the WLI field between the alternately repeated WLI field and IR field in order to suppress luminance unevenness of the normal light image. Note that the first period TE1' is the same period as the entire line exposure period TE1 since FIG. 3(b) illustrates the case where the current supply time is maximized as described above. Further, the entire line exposure period TE1 corresponds to a first entire line exposure period according to the present disclosure.

On the other hand, when operating the second light source 32, the control unit 94 causes the second light source 32 to emit light during a whole second period TIR' within an excitation light emission period TIR including an entire line exposure period TE2 in the IR field between the alternately repeated WLI field and IR field, a period TRB' which is at least a part of a readout period TRB, and a period TRA' which is at least a part of a readout period TRA. Note that the second period TIR' is the same period as the excitation light emission period TIR since FIG. 3(b) illustrates the case where the current supply time is maximized as described above. Further, the entire line exposure period TE2 corresponds to a second entire line exposure period according to the present disclosure.

Here, the readout period TRB is a readout period TR that is adjacent to the entire line exposure period TE2 and is previous to the entire line exposure period TE2 in a time series. In addition, in the first embodiment, the period TRB' is a period from a timing P1' after a timing P1 at which a horizontal line located at the center among all the horizontal lines of the image sensor 522 starts exposure to a start timing of the entire line exposure period TE2.

In addition, the readout period TRA is a readout period TR that is adjacent to the entire line exposure period TE2 and is subsequent to the entire line exposure period TE2 in a time series. In addition, in the first embodiment, the period TRA' is a period from an end timing of the entire line exposure period TE2 to a timing P2' before a timing P2 at which the horizontal line located at the center among all the horizontal lines of the image sensor 522 ends exposure.

For example, when the image sensor 522 is an NTSC type image sensor, the entire line exposure period TE is 8.0 ms. Further, when a current supply time at a performance limit at which a current may be continuously supplied at the maximum current value during overdrive driving is 12.0 ms, the periods TRB' and TRA' are 2.0 ms, respectively, in the second light source 32. Note that the overdrive driving is a scheme in which a current exceeding a current value flowing during steady light emission of an illumination, such as an LED, is caused to flow for a certain period of time such that the illumination instantaneously emits light more brightly.

In addition, for example, in a case where the image sensor 522 is a PAL type image sensor, the entire line exposure period TE is 10.0 ms. Further, when the current supply time at the above-described performance limit in the second light source 32 is 12.0 ms, the periods TRB' and TRA' are 1.0 ms, respectively. Note that, in the case where the image sensor 522 is the PAL type image sensor, the balance in brightness between the normal light image and the fluorescence image is set to match with that of the NTSC type image sensor, and thus, the maximum value of the first period TE1' may be a period (For example, 8.0 ms) shorter than 10.0 ms of the entire line exposure period TE.

According to the first embodiment described above, the following effects are achieved.

When controlling the operation of the second light source 32, the control device 9 according to the first embodiment causes the second light source 32 to emit light during the whole second period TIR' described above. That is, a light emission amount of the excitation light may be increased as compared with the known technique in which excitation light is emitted only in the entire line exposure period TE2. As a result, the luminance of fluorescence associated with the excitation light may be increased, and the brightness of the fluorescence image may be sufficiently secured. Here, the fluorescence accompanying the excitation light from the second light source 32 leaks into the WLI field, but the image quality of the normal light image is hardly affected since the fluorescence is considerably darker than the normal light.

Therefore, it is possible to generate an image (normal light image and fluorescence image) suitable for observation with the control device 9 according to the first embodiment.

Second Embodiment

Next, a second embodiment will be described.

In the following description, the same reference signs are given to the same configurations as those of the above-described first embodiment, and a detailed description thereof will be omitted or simplified.

In the second embodiment, when operating the second light source 32, the control unit 94 executes control different from the light source control described in the first embodiment.

The control unit 94 according to the second embodiment specifies a position of a fluorescence area including a pixel whose pixel level is higher than a specific threshold in a fluorescence image. That is, the control unit 94 has a function as an area specifying unit according to the present disclosure. Here, as the pixel level, a luminance value or an RGB value (pixel value) according to a Y signal (luminance signal) may be exemplified. In the second embodiment, the luminance value is adopted as the pixel level.

Further, the control unit 94 executes any one of first excitation light emission control to third excitation light emission control based on the position of the fluorescence area. Specifically, in a case where the position of the fluorescence area is located in the upper part inside the fluorescence image, the control unit 94 executes the first excitation light emission control. In addition, in a case where the position of the fluorescence area is located in the lower part inside the fluorescence image, the control unit 94 executes the second excitation light emission control. In addition, in a case where the position of the fluorescence area is located at vertical center inside the fluorescence image, the control unit 94 executes the third excitation light emission control.

Figure 4:
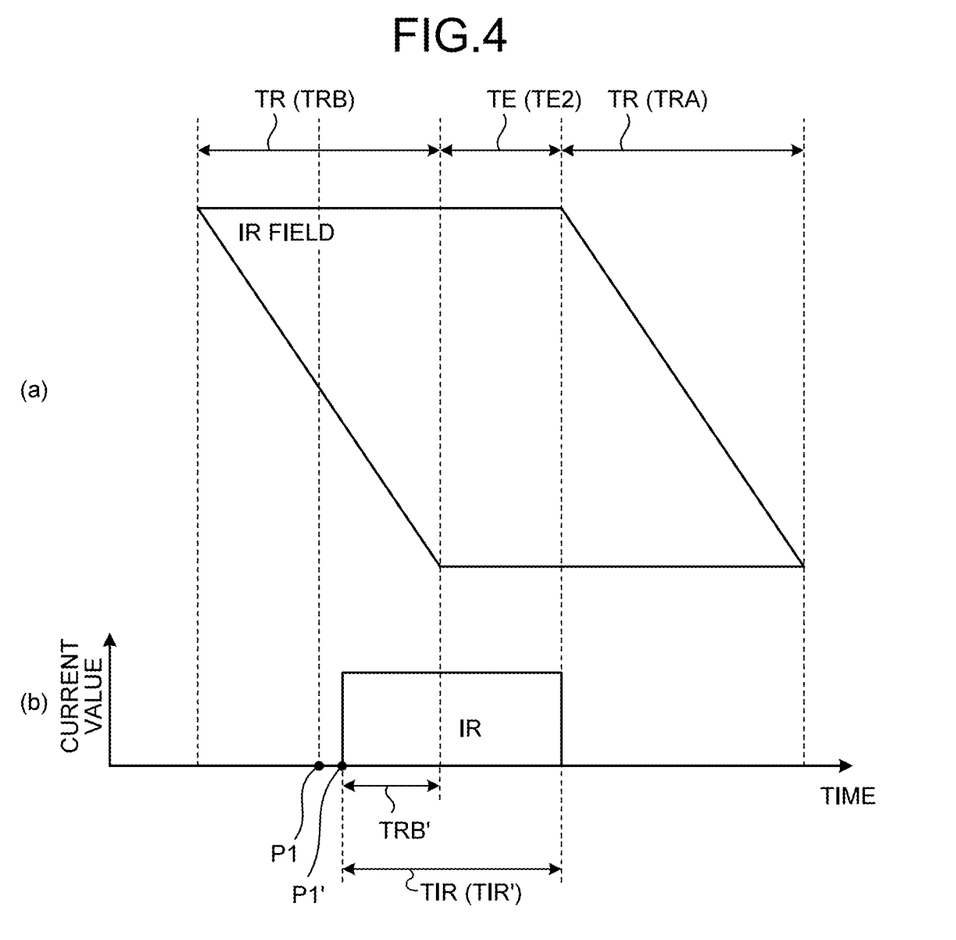
FIG. 4 is a view illustrating first excitation light emission control executed by a control unit according to a second embodiment.
Figure 5:
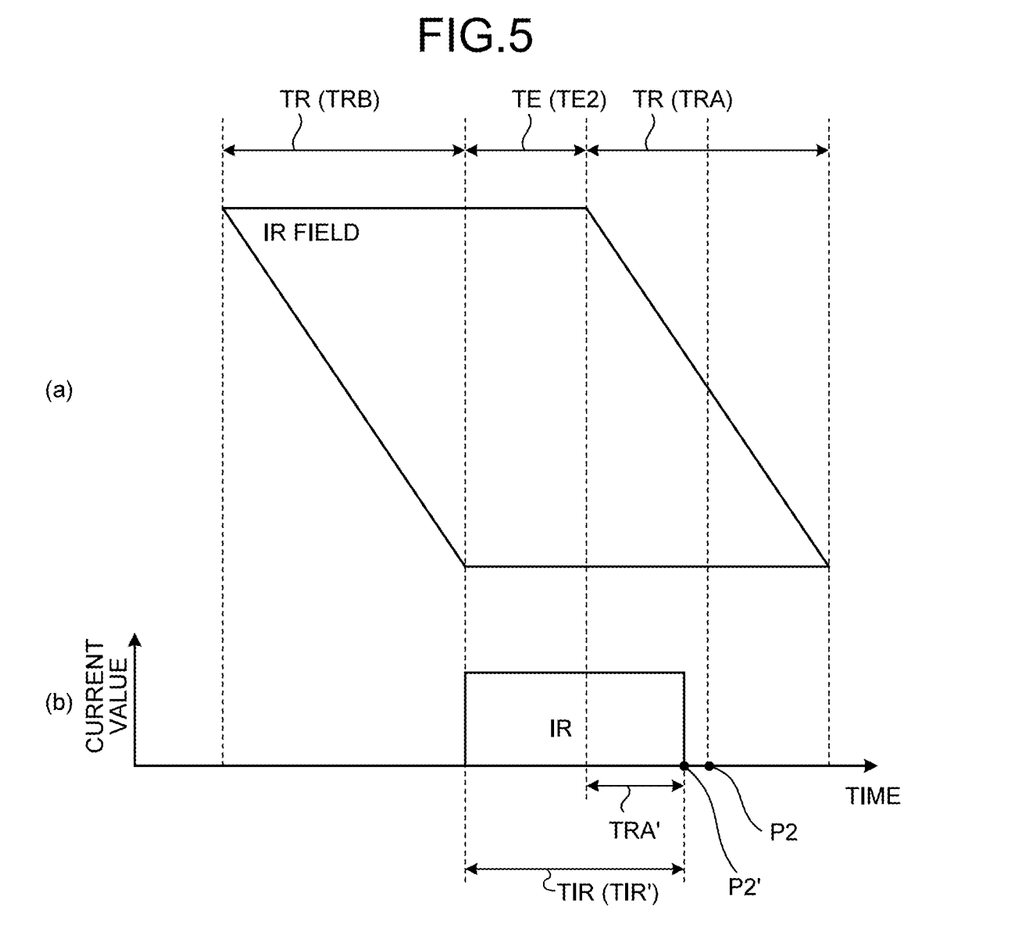
FIG. 5 is a view illustrating second excitation light emission control executed by the control unit according to the second embodiment.
Figure 6:
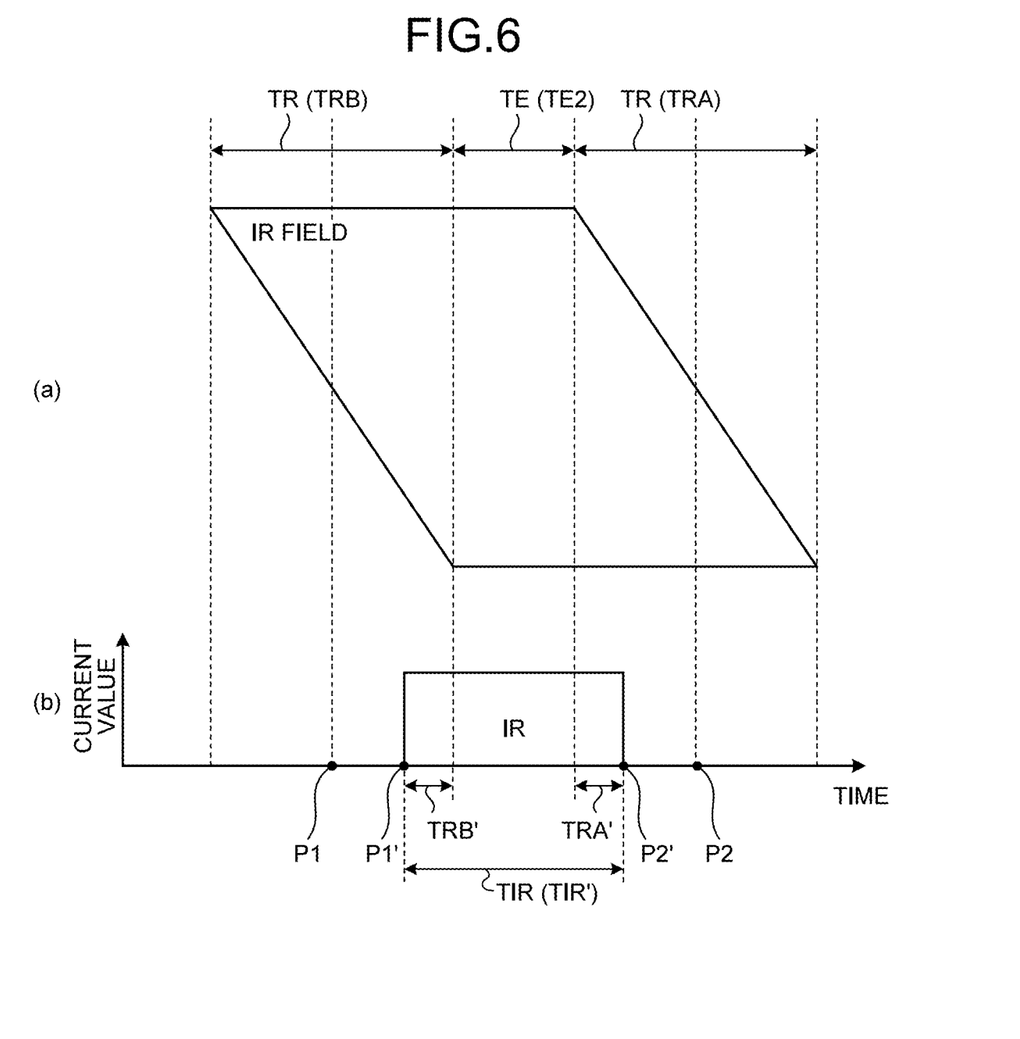
FIG. 6 is a view illustrating third excitation light emission control executed by the control unit according to the second embodiment.

FIG. 4 is a view for describing the first excitation light emission control executed by the control unit 94. FIG. 5 is a view for describing the second excitation light emission control executed by the control unit 94. FIG. 6 is a view for describing the third excitation light emission control executed by the control unit 94. Specifically, FIGS. 4 to 6 are the views corresponding to FIG. 3. Note that FIGS. 4 to 6 illustrate only the IR field for convenience of the description.

Specifically, the first excitation light emission control is control to cause the second light source 32 to emit light during a whole second period TIR' within an excitation light emission period TIR including an entire line exposure period TE2 in the IR field and a period TRB' which is at least a part of a readout period TRB as illustrated in FIG. 4. Note that the second period TIR' is the same period as the excitation light emission period TIR since FIG. 4(b) illustrates the case where the current supply time is maximized similarly to FIG. 3. In addition, the period TRB' is a period obtained by adding the period TRB' and the period TRA' described in the first embodiment since FIG. 4(b) illustrates a current supply time at a performance limit in the second light source 32. Note that the period TRB' illustrated in FIG. 4(b) is also a period from a timing P1' after a timing P1 at which a horizontal line located at the center among all horizontal lines of the image sensor 522 starts exposure to a start timing of the entire line exposure period TE2, which is similar to the period TRB' described in the first embodiment.

In addition, the second excitation light emission control is control to cause the second light source 32 to emit light during a whole second period TIR' within an excitation light emission period TIR including the entire line exposure period TE2 in the IR field and a period TRA' which is at least a part of a readout period TRA as illustrated in FIG. 5. Note that the second period TIR' is the same period as the excitation light emission period TIR since FIG. 5(b) illustrates the case where the current supply time is maximized similarly to FIG. 3. In addition, the period TRA' is a period obtained by adding the period TRB' and the period TRA' described in the first embodiment since FIG. 5(b) illustrates a current supply time at a performance limit in the second light source 32. Note that the period TRA' illustrated in FIG. 5(b) is also a period from an end timing of the entire line exposure period TE2 to a timing P2' before a timing P2 at which the horizontal line located at the center among all the horizontal lines of the image sensor 522 ends exposure, which is similar to the period TRA' described in the first embodiment.

Further, the third excitation light emission control is similar to the light source control described in the first embodiment as illustrated in FIG. 6.

According to the second embodiment described above, not only the same effects as those in the above-described first embodiment but also the following effects are obtained.

The control device 9 according to the second embodiment executes any one of the first excitation light emission control to the third excitation light emission control based on the position of the fluorescence area. That is, it is possible to brighten the fluorescence area located in the upper part inside the fluorescence image by executing the first excitation light emission control. In addition, it is possible to brighten the fluorescence area located in the lower part inside the fluorescence image by executing the second excitation light emission control. In addition, it is possible to brighten the fluorescence area located at the vertical center inside the fluorescence image by executing the third excitation light emission control.

Therefore, the fluorescence area may be made brighter with the control device 9 according to the second embodiment, so that a fluorescence image suitable for observation may be generated.

Other Embodiments

The modes for carrying out the present disclosure have been described hereinbefore. However, the present disclosure is not limited only to the first and second embodiments described above.

In the first embodiment described above, the excitation light emission period TIR (second period TIR') may be a period including the whole readout period TRB, the entire line exposure period TE2, and the whole readout period TRA.

Similarly, the excitation light emission period TIR (second period TIR') in the first excitation light emission control may be a period including the whole readout period TRB and the entire line exposure period TE2 in the second embodiment described above. In addition, the excitation light emission period TIR (second period TIR') in the second excitation light emission control may be a period including the entire line exposure period TE2 and the whole readout period TRA.

In the first and second embodiments described above, the period TRB' and the period TRA' may be different periods.

Although the third excitation light emission control described in the second embodiment is executed in the above-described first embodiment, the present disclosure is not limited thereto, and either the first excitation light emission control or the second excitation light emission control described in the second embodiment may be executed.

In the second embodiment described above, any one of the first excitation light emission control to the third excitation light emission control may be executed based on the brightness (average value of luminance values or the like) of a specific area (detection area) in the normal light image or the fluorescence image.

Meanwhile, photo-dynamic diagnosis (PDD), which is one of cancer diagnosis methods for detecting a cancer cell, is known.

In the photodynamic diagnosis, for example, a photosensitive substance such as 5-aminolevulinic acid (hereinafter, referred to as 5-ALA) is used. The 5-ALA is a natural amino acid originally contained in living organisms of animals and plants. This 5-ALA is taken into a cell after administration in vivo, and is biosynthesized into protoporphyrin in mitochondria. Further, the protoporphyrin is excessively accumulated in a cancer cell. In addition, the protoporphyrin excessively accumulated in the cancer cell has photoactivity. Therefore, the protoporphyrin emits fluorescence (for example, red fluorescence in a wavelength band of 600 nm to 740 nm) when being excited with excitation light (for example, blue visible light in a wavelength band of 375 nm to 445 nm). In this manner, a cancer diagnostic method in which a cancer cell is caused to emit fluorescence using a photosensitizer is referred to as the photo-dynamic diagnosis.

Further, in the first and second embodiments described above, the first light source 31 may be configured using an LED that emits white light, and the second light source 32 may be configured using a semiconductor laser that emits excitation light for exciting protoporphyrin (for example, blue visible light in a wavelength band of 375 nm to 445 nm). Even in the case of adopting such a configuration, the same effects as those of the first and second embodiments described above may be obtained.

Although the first and second periods are set to be alternately repeated in the first and second embodiments described above, the present disclosure is not limited thereto, and at least one of the first and second periods may be continuous such that a frequency ratio between the first and second periods is a ratio other than 1:1.

Although the light source control device according to the present disclosure is mounted on the medical observation system 1 in which the insertion unit 2 is configured using the rigid endoscope in the first and second embodiments described above, the present disclosure is not limited thereto. For example, the light source control device according to the present disclosure may be mounted on a medical observation system in which the insertion unit 2 is configured using a flexible endoscope. In addition, the light source control device according to the present disclosure may be mounted on a medical observation system such as a surgical microscope (see, for example, JP 2016-42981 A) that enlarges and observes a predetermined visual field area in a subject (in a living body) or a subject surface (living body surface).

A part of the configuration of the camera head 5 or a part of the configuration of the control device 9 may be provided in, for example, the connector CN1 or the connector CN2 in the first and second embodiments described above.

Note that the following configuration also belongs to the technical scope of the present disclosure.

(1) A light source control device includes a light source controller that causes a first light source to emit light in a visible wavelength band in a first entire line exposure period, which is an entire line exposure period in which all horizontal lines in an effective pixel area are simultaneously exposed, in a rolling shutter type image sensor in which a plurality of pixels are two-dimensionally arrayed in units of the horizontal lines, and causes a second light source to emit excitation light in a second entire line exposure period, which is the entire line exposure period different from the first entire line exposure period, and the light source controller causes the excitation light to be emitted in an excitation light emission period including the second entire line exposure period and a period, which is adjacent to the second entire line exposure period and is at least a part of a readout period during which charges accumulated in the plurality of pixels are read out, when controlling an operation of the second light source.

(2) The light source control device according to (1), in which the excitation light emission period is a period including a period that is at least a part of the readout period previous to the second entire line exposure period in a time series, and the second entire line exposure period.

(3) The light source control device according to (2), in which the excitation light emission period is a period from a timing after a timing at which a horizontal line located at a center among all the horizontal lines starts exposure to an end timing of the second entire line exposure period.

(4) The light source control device according to (1), in which the excitation light emission period is a period including the second entire line exposure period and a period that is at least a part of the readout period subsequent to the second entire line exposure period in a time series.

(5) The light source control device according to (4), in which the excitation light emission period is a period from a start timing of the second entire line exposure period to a timing before a timing at which a horizontal line located at a center among all the horizontal lines ends exposure.

(6) The light source control device according to (1), in which the excitation light emission period is a period including the second entire line exposure period, a period, which is at least a part of the readout period previous to the second entire line exposure period in a time series, and a period which is a least a part of the readout period subsequent to the second entire line exposure period in a time series.

(7) The light source control device according to any one of (1) to (6), further including: an image acquisition unit that acquires a fluorescence image, obtained by irradiating an observation target with the excitation light and capturing fluorescence from the observation target excited by the excitation light by an imaging unit; and an area specifying unit that specifies a position of a fluorescence area including a pixel whose pixel level depending on the fluorescence is higher than a specific threshold out of an entire image area in the fluorescence image, in which the light source controller executes any of first excitation light emission control for emitting the excitation light in the excitation light emission period, which includes the second entire line exposure period and a period that is at least a part of the readout period previous to the second entire line exposure period in a time series, based on the position of the fluorescence area, second excitation light emission control for emitting the excitation light in the excitation light emission period, which includes the second entire line exposure period and a period that is at least a part of the readout period subsequent to the second entire line exposure period in a time series, and third excitation light emission control for emitting the excitation light in the excitation light emission period which includes the second entire line exposure period, a period that is at least a part of the readout period previous to the second entire line exposure period in a time series, and a period that is at least a part of the readout period subsequent to the second entire line exposure period in a time series.

(8) A medical observation system including: an imaging device including a rolling shutter type image sensor in which a plurality of pixels are two-dimensionally arrayed in units of horizontal lines; a first light source that emits light in a visible wavelength band; a second light source that emits excitation light; and a light source control device that controls the first light source and the second light source, in which the light source control device includes a light source controller that causes the first light source to emit the light in the visible wavelength band in a first entire line exposure period, which is an entire line exposure period in which all horizontal lines in an effective pixel area are simultaneously exposed, in the image sensor, and causes the second light source to emit the excitation light in a second entire line exposure period, which is the entire line exposure period different from the first entire line exposure period, and the light source controller causes the excitation light to be emitted in an excitation light emission period including the second entire line exposure period and a period, which is adjacent to the second entire line exposure period and is at least a part of a readout period during which charges accumulated in the plurality of pixels are read out, when controlling an operation of the second light source.

With a light source control device and a medical observation system according to the present disclosure, it is possible to generate an image suitable for observation.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A light source control device comprising
a light source control circuitry configured to:
   cause a first light source to emit light in a visible wavelength band in a first entire line exposure period in which all horizontal lines in an effective pixel area are simultaneously exposed, in a rolling shutter type image sensor in which a plurality of pixels are two-dimensionally arrayed in units of the horizontal lines, the first entire line exposure period being a visible light emission period for a single frame;
   cause a second light source to emit excitation light in a second entire line exposure period, different from the first entire line exposure period, in which all horizontal lines in the effective pixel area are simultaneously exposed;
   cause the excitation light to be emitted in an excitation light emission period including the second entire line exposure period in which all horizontal lines in an effective pixel area are simultaneously exposed and a period, which is adjacent to the second entire line exposure period and is at least a part of a readout period during which charges accumulated in the plurality of pixels are read out, when controlling an operation of the second light source, the excitation light emission period being for a single frame; and
   switch between the excitation light emission period and the visible light emission period, wherein the excitation light emission period for excitation light within a single frame is longer than the visible light emission period for visible light within a single frame.

2. The light source control device according to claim 1, wherein the at least part of the readout period of the excitation light emission period includes at least a part of a readout period previous to the second entire line exposure period in a time series.

3. The light source control device according to claim 2, wherein the excitation light emission period includes a period from a timing after exposure of a horizontal line at a center among all the horizontal lines starts to an end of the second entire line exposure period.

4. The light source control device according to claim 1, wherein the at least part of the readout period of the excitation light emission period includes at least a part of a readout period subsequent to the second entire line exposure period in a time series.

5. The light source control device according to claim 4, wherein the excitation light emission period includes a period from a start of the second entire line exposure period to an end of exposure of a horizontal line at a center among all the horizontal lines.

6. The light source control device according to claim 1, wherein the excitation light emission period includes the second entire line exposure period, a period, which is at least a part of a readout period previous to the second entire line exposure period in a time series, and a period which is at least a part of a readout period subsequent to the second entire line exposure period in a time series.

7. The light source control device according to claim 1, further comprising:
   an image acquisition circuitry configured to acquire a fluorescence image, obtained by irradiating an observation target with the excitation light and capturing fluorescence from the observation target excited by the excitation light by an image sensor; and
   an area specifying circuitry configured to specify a position of a fluorescence area including a pixel whose pixel level depending on the fluorescence is higher than a specific threshold out of an entire image area in the fluorescence image, wherein the light source control circuitry is configured to execute any of:

first excitation light emission control for emitting the excitation light in the excitation light emission period, which includes the second entire line exposure period and a period that is at least a part of the readout period previous to the second entire line exposure period in a time series, based on the position of the fluorescence area;

second excitation light emission control for emitting the excitation light in the excitation light emission period, which includes the second entire line exposure period in which all horizontal lines in an effective pixel area are simultaneously exposed and a period that is at least a part of the readout period subsequent to the second entire line exposure period in a time series; and third excitation light emission control for emitting the excitation light in the excitation light emission period which includes the second entire line exposure period, a period that is at least a part of the readout period previous to the second entire line exposure period in a time series, and a period that is at least a part of the readout period subsequent to the second entire line exposure period in a time series.

8. A medical observation system comprising:

an image sensor including a rolling shutter type image sensor in which a plurality of pixels are two-dimensionally arrayed in units of horizontal lines;

a first light source configured to emit light in a visible wavelength band;

a second light source configured to emit excitation light; and a light source control circuit configured to control the first light source and the second light source, the light source control circuit being configured to cause the first light source to emit the light in the visible wavelength band in a first entire line exposure period in which all horizontal lines in an effective pixel area are simultaneously exposed, in the image sensor, the first entire line exposure period being a visible light emission period for a single frame, cause the second light source to emit the excitation light in a second entire line exposure period, different from the first entire line exposure period, in which all horizontal lines in the effective pixel area are simultaneously exposed, cause the excitation light to be emitted in an excitation light emission period including the second entire line exposure period in which all horizontal lines in an effective pixel area are simultaneously exposed and a period, which is adjacent to the second entire line exposure period and is at least a part of a readout period during which charges accumulated in the plurality of pixels are read out, when controlling an operation of the second light source, the excitation light emission period being for a single frame; and switch between the excitation light emission period and the visible light emission period, wherein the excitation light emission period for excitation light within a single frame is longer than visible light emission period for visible light within a single frame.

9. The medical observation system according to claim 8, wherein the excitation light emission period includes a period that is at least a part of a readout period previous to the second entire line exposure period in a time series, and the second entire line exposure period.

10. The medical observation system according to claim 9, wherein the excitation light emission period includes a period from a timing after exposure of a horizontal line at a center among all the horizontal lines starts to an end of the second entire line exposure period.

11. The medical observation system according to claim 8, wherein the excitation light emission period includes the second entire line exposure period and a period that is at least a part of a readout period subsequent to the second entire line exposure period in a time series.

12. The medical observation system according to claim 11, wherein the excitation light emission period includes a period from a start of the second entire line exposure period to an end of exposure of a horizontal line at a center among all the horizontal lines ends exposure.

13. The medical observation system according to claim 8, wherein the excitation light emission period includes the second entire line exposure period, a period, which is at least a part of the readout period previous to the second entire line exposure period in a time series, and a period which is at least a part of the readout period subsequent to the second entire line exposure period in a time series.

14. The medical observation system according to claim 8, further comprising:

an image acquisition circuitry configured to acquire a fluorescence image, obtained by irradiating an observation target with the excitation light and capturing fluorescence from the observation target excited by the excitation light by the image sensor; and an area specifying circuitry configured to specify a position of a fluorescence area including a pixel whose pixel level depending on the fluorescence is higher than a specific threshold out of an entire image area in the fluorescence image, wherein the light source control circuit is configured to execute any of:

first excitation light emission control for emitting the excitation light in the excitation light emission period, which includes the second entire line exposure period and a period that is at least a part of the readout period previous to the second entire line exposure period in a time series, based on the position of the fluorescence area;

second excitation light emission control for emitting the excitation light in the excitation light emission period, which includes the second entire line exposure period and a period that is at least a part of the readout period subsequent to the second entire line exposure period in a time series; and third excitation light emission control for emitting the excitation light in the excitation light emission period which includes the second entire line exposure period in which all horizontal lines in an effective pixel area are simultaneously exposed, a period that is at least a part of the readout period previous to the second entire line exposure period in a time series, and a period that is at least a part of the readout period subsequent to the second entire line exposure period in a time series.

15. A method for controlling a light source, comprising
controlling a first light source to emit light in a visible wavelength band in a first entire line exposure period in which all horizontal lines in an effective pixel area are simultaneously exposed, in a rolling shutter type image sensor in which a plurality of pixels are two-dimensionally arrayed in units of the horizontal lines, the first entire line exposure period being a visible light emission period for a single frame;
controlling a second light source to emit excitation light for an excitation light emission period for a single frame, the excitation light emission period including a second entire line exposure period, different from the first entire line exposure period, in which all horizontal lines in the effective pixel area are simultaneously exposed, and a period, which is adjacent to the second entire line exposure period and is at least a part of a readout period during which charges accumulated in the plurality of pixels are read out, and
switching between the excitation light emission period and the visible light emission period, wherein the excitation light emission period for excitation light within a single frame is longer than visible light emission period for visible light within a single frame.

16. The method according to claim 15, wherein the excitation light emission period includes a period that is at least a part of a readout period previous to the second entire line exposure period in a time series, and the second entire line exposure period.

17. The method according to claim 16, wherein the excitation light emission period includes a period from a timing after exposure of a horizontal line at a center among all the horizontal lines starts to an end of the second entire line exposure period.

18. The method according to claim 15, wherein the excitation light emission period includes the second entire line exposure period and a period that is at least a part of a readout period subsequent to the second entire line exposure period in a time series.

19. The method according to claim 15, wherein the excitation light emission period includes a period from a start of the second entire line exposure period to an end of exposure of a horizontal line at a center among all the horizontal lines ends exposure.

20. The method according to claim 15, wherein the excitation light emission period includes the second entire line exposure period, a period, which is at least a part of a readout period previous to the second entire line exposure period in a time series, and a period which is at least a part of a readout period subsequent to the second entire line exposure period in a time series.

* * * * *